United States Patent [19]
Okada et al.

[11] Patent Number: 6,140,097
[45] Date of Patent: Oct. 31, 2000

[54] MESOPHILIC XYLANASES

[75] Inventors: Gentaro Okada; Takanori Nihira, both of Shizuoka; Shoji Gotoh, Iruma-gun; Masako Mizuno, Awa-gun; Toshiaki Kono, Tama; Takashi Yamanobe, Ushiku, all of Japan

[73] Assignees: Meiji Seika Kaisha Ltd.; Japan as represented by Director General of Agency of Industrial Science and Technology, both of Tokyo, Japan

[21] Appl. No.: 09/171,850

[22] PCT Filed: Mar. 3, 1998

[86] PCT No.: PCT/JP98/00869

§ 371 Date: Nov. 16, 1998

§ 102(e) Date: Nov. 16, 1998

[87] PCT Pub. No.: WO98/39423

PCT Pub. Date: Sep. 11, 1998

[30] Foreign Application Priority Data

Mar. 4, 1997 [JP] Japan ..................... 9-063957

[51] Int. Cl.⁷ ............... C12N 9/00; C12N 9/24; C12N 9/42
[52] U.S. Cl. .............. 435/209; 435/183; 435/200
[58] Field of Search .................... 435/183, 195, 435/200, 203, 209

[56] References Cited

U.S. PATENT DOCUMENTS 4,742,005  5/1988  Yamanobe et al. .
4,956,291  9/1990  Yamanobe et al. .

FOREIGN PATENT DOCUMENTS 1-21957    4/1989  Japan .
1-171484   7/1989  Japan .
1-171485   7/1989  Japan .
4-117244   4/1992  Japan .
7-236431   9/1995  Japan .

OTHER PUBLICATIONS

Yamanobe et al., "Purification and Some Properties of a Microcrystalline Cellulose–hydrolyzing Enzyme (Avicelase II) from Fugal Strain Y–94", *Agric. Biol. Chem.,* 52(10), 2493–2501 (1988).

Yamanobe et al., "Purification and Properties of a β–Glucosidase from Fungal Strain Y–94", *Agric. Biol. Chem.,* 53(12), 3359–3360 (1989).

Yamanobe et al., "Some Enzymatic Properties of Endo–1 4–β–glucanase Components from Fungal Strain Y–94", *Agric. Biol. Chem.,* 54(2), 309–317 (1990).

Yamanobe et al., "Isolation of a Cellulolytic Enzyme Producing Microorganism, Culture Conditions and Some Properties of the Enzymes", *Agric. Biol. Chem.,* 51(1), 65–74 (1987).

Mitsuishi et al., "Purification and Properties of Thermostable Xylanases from Mesophilic Fungus Strain Y–94", *Agric. Biol. Chem.,* 51(12), 3207–3213 (1987).

Mitsuishi et al., "Two thermostable β–xylosidases from the mesophilic fungal strain Y–94", *Report of National Institute of Bioscience and Human–Technology,* 1(1), 37–44 (1993).

Hayashi et al, "Purification and Properties of a Low–Temperature–Active Enzyme Degrading Both Cellulose and Xylan from Acremonium Alcalophilum JCM 7366", Seibutsukogakukaishi, A. alcalophilum JCM 7366, vol. 75, No. 1, pp. 9–14, 1997.

Hayashi et al, Low–Temperature–Active Cellulase Produced by Acremonium Alcalophilum JCM 7366, Seibutsukogakukaishi, A. alcalophilum, vol. 74, No. 1, pp. 7–10 (1996).

*Primary Examiner*—Ponnathapu Achutamurthy
*Assistant Examiner*—Manjunath Rao
*Attorney, Agent, or Firm*—Frishauf, Holtz, Goodman, Langer & Chick, P.C.

[57] ABSTRACT

Mesophilic xylanases derived from *Acremonium cellulolyticus*. A mesophilic xylanase I, derived from the mold *Acremonium cellulolyticus*, capable of non-specifically hydrolyzing xylan mainly into xylose, xylobiose and xylotriose, having an optimal pH at 3.5 and an optimal temperature for action at 55° C. as determined by saccharifying activity for soluble xylan as a substrate and a molecular weight of 30,000 as determined by SDS-polyacrylamide gel electrophoresis. A mesophilic xylanase II having an optimal pH a 3.8, an optimal temperature for action at 55° C. and a molecular weight of 25,500. A mesophilic xylanase III having an optimal pH at 3.5, an optimal temperature for action at 50° C. and a molecular weight of 33,500.

3 Claims, 5 Drawing Sheets

MESOPHILIC XYLANASES

TECHNICAL FIELD

The present invention relates to xylanases, particularly to novel mesophilic xylanases derived from a mold *Acremonium cellulolyticus*.

BACKGROUND ART

Xylan is one of the polysaccharides widely existing in nature, and is classified as hemicellulose among polysaccharides, which are the main constituents of cell walls and peripheral tissues of higher plants, such as cellulose, lignin, hemicelluloses, and pectins. The structure is high-molecular-weight polysaccharide having a main chain polymerized by a β-1,4-xyloside bond with xylose being a unit. In nature, xylan exists not only as homoxylan whose constituent sugar is only xylose but also as heteroxylan such as arabinoxylan in which arabinose branches and is bound to the main chain.

Xylanase is the general name for enzymes catalyzing the hydrolysis of xylan via xylosaccharides and xylobiose finally into xylose, and is roughly categorized into endoxylanase, exoxylanase, and β-xylosidase depending on the action modes. Detailed comparison of these action modes establishes a large kind of enzymes. Therefore, it has been thought that xylan in plant tissues is degraded by a synergistic action of xylanases having a variety of action modes.

Xylanase is utilized for production of xylooligosaccharides or xylose from xylan or a treatment of a biomass. In addition, recently, application of xylanase is progressing in the field of enzymes for feeds and food processing, and various kinds of xylanase are under research and development.

A mold *Acremonium cellulolyticus* has a property that it produces a cellulase having strong saccharification, and usefulness for feed and silage is reported (See e.g. Japanese Patent Laid-open Pub. Nos. Hei 4-117244 and Hei 7-236431). Cellulase component contained therein is also reported (See e.g. Agric. Biol. Chem. 52, 2493–2501 (1988); ibid. 53, 3359–3360 (1989); ibid. 54, 309–317 (1990)). In addition, the crude enzyme produced by said mold produces xylanase together with cellulase, and some components of the xylanase were reported (See e.g. Agric. Biol. Chem. 51, 65–74 (1987); ibid. 51, 3207–3213 (1987); Report of National Institute of Bioscience and Human-Technology, 1, 37–44 (1993), Japanese Patent Pub. No. Hei 1-21957; and Japanese Patent Laid-open Pub. Nos. Hei 1-171484 and Hei 1-171485).

These reports relate to thermostable xylanase and xylooligosyl transferase, and mesophilic xylanase was not known in detail.

It is preferable to use mesophilic xylanase having an activity from neutral to acidic region and in the mesophilic region, the optimal temperature being up to about 60° C. when it is applied for food or feed. Such mesophilic xylanase, however, has not been known so far.

DISCLOSURE OF THE INVENTION

The inventors conducted exhaustive fractionation/purification of various enzymes constituting the xylanase system derived from *Acremonium cellulolyticus* so that they found novel active components having optimal activities at the mesophilic region in the enzymes. Based on this finding, the present invention was completed. The object of the present invention is to provide novel mesophilic xylanases effective for food processing, feed, silage, and other purposes.

The present invention provides mesophilic Xylanase I, derived from a mold *Acremonium cellulolyticus*, having the following properties:

(a) action: non-specifically hydrolyzing xylan mainly into xylose, xylobiose, xylotriose and so on, (b) substrate specificity: the enzyme acts on xylan, (c) optimal pH and stable pH range: optimal pH is 3.5, stable within pH 3.5–9.5 (25° C., 2 hours) as determined by saccharifying activity using soluble xylan as a substrate, (d) optimal temperature for action: 55° C. as determined by saccharifying activity using soluble xylan as the substrate, (e) temperature-stability: stable at 55° C. or lower (pH 3.5, 10 min), (f) molecular weight: 30,000 as determined by SDS-polyacrylamide gel electrophoresis, 69,500 as determined by gel filtration chromatography, (g) specific activity: 112.1 U/mg-protein as determined by saccharifying activity for soluble xylan, 76.6 U/mg-protein as determined by saccharifying activity for insoluble xylan.

The present invention also provides mesophilic Xylanase II, derived from the mold *Acremonium cellulolyticus*, having following properties:

(a) action: non-specifically hydrolyzing xylan mainly into xylose, xylobiose, xylotriose and so on, (b) substrate specificity: the enzyme acts on xylan, (c) optimal pH and stable pH range: optimal pH is 3.8, stable within pH 3.0–9.5 (25° C., 2 hours) as determined by saccharifying activity using soluble xylan as a substrate, (d) optimal temperature for action: 55° C. as determined by saccharifying activity using soluble xylan as a substrate, (e) temperature-stability: stable at 55° C. or lower (pH 3.5, 10 min), (f) molecular weight: 25,500 as determined by SDS-polyacrylamide gel electrophoresis, 58,000 as determined by gel filtration chromatography, (g) specific activity: 86.1 U/mg-protein as determined by saccharifying activity for soluble xylan, 87.6 U/mg-protein as determined by saccharifying activity for insoluble xylan.

The present invention further provides mesophilic Xylanase III, derived from the mold *Acremonium cellulolyticus*, having following properties:

(a) action: non-specifically hydrolyzing xylan mainly into xylose, xylobiose, xylotriose and so on, (b) substrate specificity: the enzyme acts on xylan, (c) optimal pH and stable pH range: optimal pH is 3.5, stable within pH 2.5–9.5 (25° C., 2 hours) as determined by saccharifying activity using soluble xylan as a substrate, (d) optimal temperature for action: 50° C. as determined by saccharifying activity using soluble xylan as a substrate, (e) temperature-stability: stable at 50° C. or lower (pH 3.5, 10 min), (f) molecular weight: 33,500 as determined by SDS-polyacrylamide gel electrophoresis, 23,000 as determined by gel filtration chromatography, (g) specific activity: 74.8 U/mg-protein as determined by saccharifying activity for soluble xylan, 101.5 U/mg-protein as determined by saccharifying activity for insoluble xylan.

BRIEF DESCRIPTION OF THE DRAWINGS

FIGS. 1a, 1b and 1c indicate the optimal pH of mesophilic Xylanases I, II, and III, respectively.

FIGS. 2a, 2b and 2c indicate the ranges of stable pH of Xylanases I, II, and III, respectively.

FIGS. 3a, 3b and 3c are graphs which show the optimal temperatures of mesophilic Xylanases I, II, and III, respectively.

BEST MODE FOR CARRYING OUT THE INVENTION

Figure 1A:
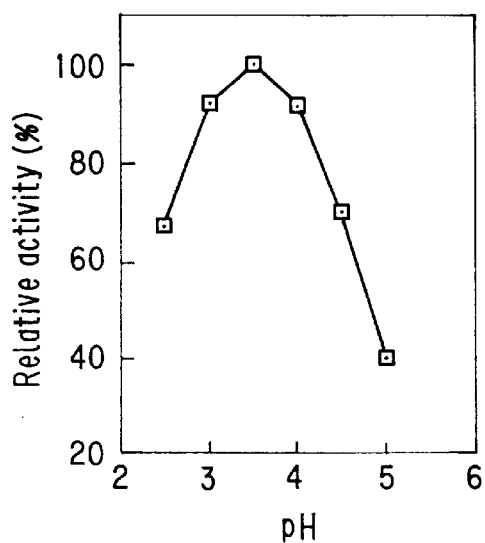
FIGS. 1a, 1b and 1c are graphs which show the optimal pH of the enzymes.

Mesophilic xylanases I–III according to the present invention are active components contained in the xylanase system produced by *Acremonium cellulolyticus*. The present invention will be described in detail hereafter.

The microorganisms producing the xylanase system containing the mesophilic xylanases according to the present invention include *Acremonium cellulolyticus* TN strain and *Acremonium cellulolyticus* strain.

The former microorganism *Acremonium cellulolyticus* TN strain was deposited in Fermentation Research Institute, Agency of Industrial Science and Technology, Ministry of International Trade and Industry of 1–3, Higashi 1-chome, Yatabe-machi, Tsukuba-gun, Ibaraki-ken, Japan (at present, however, although residing at the same place, the address was changed into 1–3, Higashi 1-chome, Tsukuba-shi, Ibaraki-ken, Japan; and the name was changed into National Institute of Bioscience and Human-Technology, Agency of Industrial Science and Technology, Ministry of International Trade and Industry), according to the international treaty, with the deposition code of FERM BP-685 (transferred on Dec. 20, 1984 from the original deposit).

This original deposit was done on Oct. 13, 1984 in the Fermentation Research Institute, Agency of Industrial Science and Technology, Ministry of International Trade and Industry with the deposition code of FERM 7894.

The latter microorganism *Acremonium cellulolyticus* strain was deposited in the National Institute of Bioscience and Human-Technology, Agency of Industrial Science and Technology, Ministry of International Trade and Industry of 1–3, Higashi 1-chome, Tsukuba-shi, Ibaraki-ken, Japan (transferred from the original deposit on Feb. 19, 1997), according to the international treaty, with the deposition code of FERM BP-5826. The original deposit of this strain was done in the Fermentation Research Institute, Agency of Industrial Science and Technology, Ministry of International Trade and Industry, with the deposition code of FERM P-6867, on Jan. 12, 1983.

The xylanase system can be produced by these microorganisms according to methods described in Japanese Patent Publication No. Hei 1-21957 and Japanese Patent Publication No. Hei 1-171484, for example.

Usually a liquid medium is used containing a plant biomass such as xylan, xyloglucan, cellulose, avicel, wheat bran, rice plant straw, and/or bagasse, as carbon source(s); an organic and/or inorganic nitrogen source(s) such as peptone, yeast extract, nitrate, and/or ammonium salt; and small amounts of metal salts. Cultivation is carried out aerobically at 20–40° C. for 2–15 days.

After one of said microorganisms is cultivated, insoluble matter is separated from the resultant culture e.g. by centrifugation, the obtained supernatant (crude enzyme liquid) is concentrated e.g. by ultrafiltration, and a preservative and other additives are added to the concentrated enzyme liquid, or the concentrated enzyme liquid is dried to a powder by a spray-dry method.

Mesophilic xylanases I–III according to the present invention can be obtained by purifying the concentrated enzyme liquid or the powdered enzyme.

As purifying methods, conventional methods such as a salting-out method by ammonium sulfate or the like, precipitation using organic solvent such as alcohol, a membrane separation method, chromatography using an ion-exchanger, a carrier for hydrophobic chromatography, a carrier for gel-filtration etc., can be used singly or in combination.

Properties of highly purified mesophilic xylanases according to the present invention are described below. They are novel enzymes which have not been known in any publication so far.

Mesophilic Xylanase I
    (a) action: non-specifically hydrolyzing xylan mainly into xylose, xylobiose, xylotriose and so on,
    (b) substrate specificity: this enzyme acts on xylan,
    (c) optimal pH and stable pH range: optimal pH is 3.5 (FIG. 1a), stable within pH 3.5–9.5 (25° C., 2 hours) (FIG. 2a) as determined by saccharifying activity using soluble xylan as a substrate,
    (d) optimal temperature for action: 55° C. (FIG. 3a) as determined by saccharifying activity using soluble xylan as a substrate,
    (e) temperature-stability: stable at 55° C. or lower (pH 3.5, 10 min)(FIG. 4a),
    (f) molecular weight: 30,000 as determined by SDS-polyacrylamide gel electrophoresis (FIG. 5), 69,500 as determined by gel filtration chromatography,
    (g) specific activity: 112.1 U/mg-protein as determined by saccharifying activity for soluble xylan, 76.6 U/mg-protein as determined by saccharifying activity for insoluble xylan.

Mesophilic Xylanase II
    (a) action: non-specifically hydrolyzing xylan mainly into xylose, xylobiose, xylotriose and so on,
    (b) substrate specificity: this enzyme acts on xylan,
    (c) optimal pH and stable pH range: optimal pH is 3.8 (FIG. 1b), stable within pH 3.0–9.5 (25° C., 2 hours) (FIG. 2b) as determined by saccharifying activity using soluble xylan as a substrate,
    (d) optimal temperature for action: 55° C. (FIG. 3b) as determined by saccharifying activity using soluble xylan as a substrate,
    (e) temperature-stability: stable at 55° C. or lower (pH 3.5, 10 min)(FIG. 4b),
    (f) molecular weight: 25,500 as determined by SDS-polyacrylamide gel electrophoresis (FIG. 5), 58,000 as determined by gel filtration chromatography, (g) specific activity: 86.1 U/mg-protein as determined by saccharifying activity for soluble xylan, 87.6 U/mg-protein as determined by saccharifying activity for insoluble xylan.

Mesophilic Xylanase III
  (a) action: non-specifically hydrolyzing xylan mainly into xylose, xylobiose, xylotriose and so on,
  (b) substrate specificity: this enzyme acts on xylan,
  (c) optimal pH and stable pH range: optimal pH is 3.5 (FIG. 1c), stable within pH 2.5–9.5 (25° C., 2 hours) (FIG. 2c) as determined by saccharifying activity using soluble xylan as a substrate,
  (d) optimal temperature for action: 50° C. (FIG. 3c) as determined by saccharifying activity using soluble xylan as a substrate,
  (e) temperature-stability: stable at 50° C. or lower (pH 3.5, 10 min)(FIG. 4c),
  (f) molecular weight: 33,500 as determined by SDS-polyacrylamide gel electrophoresis (FIG. 5), 23,000 as determined by gel filtration chromatography,
  (g) specific activity: 74.8 U/mg-protein as determined by saccharifying activity for soluble xylan, 101.5 U/mg-protein as determined by saccharifying activity for insoluble xylan.

Determination of the enzyme activity and definition of one unit (U) are described below.

Saccharifying activity for insoluble xylan

An enzyme was incubated with a 2% suspension of xylan (Oat Spelts, Sigma Chem. Co. X-0627) at pH 3.5, 30° C., and the amount of enzyme forming reducing sugar equivalent to 1 μmol xylose per one minute was defined as one unit (U).

Saccharifying activity for insoluble xylan

An enzyme was incubated with a solution 0.25% soluble of xylan (Oat Spelts, Sigma Chem. Co. X-0627)(insoluble matter was removed from a boiled mixture of insoluble xylan) at pH 3.5, 30° C. and the amount of enzyme forming reducing sugar equivalent to 1 μmol xylose per one minute was defined as one unit (U).

Although the present invention is described in examples in detail below, the present invention is not limited to the examples.

EXAMPLE 1

Preparation of Crude Powder of Enzyme

Cultivation was carried out to obtain a preparation of xylanase derived from the microorganism belonging to the genus Acremonium as described below.

All the medium for the cultivation was heat-sterilized by the conventional method. Composition of the medium Cellulose 4 wt. %, dipotassium hydrogen phosphate 1.2 wt. %, Bacto Peptone 1 wt. %, potassium nitrate 0.6 wt. %, urea 0.2 wt. %, potassium chloride 0.16 wt. %, magnesium sulfate heptahydrate 0.12 wt. %, zinc sulfate heptahydrate 0.001 wt. %, manganese sulfate heptahydrate 0.001 wt. %, and cupric sulfate pentahydrate 0.001 wt. % (pH 4.0).

After *Acremonium cellulolyticus* TN strain (FERM BP-685) was inoculated into the above medium, cultivation was carried out with stirring at 30° C. for 48 hours. The obtained culture was then, as a seed, scaled up to 15 L medium, and cultivation was continued. Scale-ups were repeated finally to obtain 300 L culture in a 600 L tank, after aeration and stirring for 7 days.

The obtained culture was filtrated by a filter press, the obtained filtrate was concentrated by ultrafiltration down to 15 L, the obtained condensate was dried by a spray-dry method after addition of 2 kg lactose to give powder. 5.0 kg xylanase preparation was obtained by this procedure.

EXAMPLE 2

The crude powder obtained in Example 1 was dissolved in acetate buffer (0.02M, pH 5.5), and insoluble matter was removed using a refrigerated high-speed centrifuge. The obtained supernatant was purified as a starting material (crude enzyme) for enzyme purification according to the following means.

1) Strongly basic anion-exchange chromatography

The crude enzyme was absorbed on QAE-TOYOPEARL 550C (Tosoh Co., Ltd.), step-wise elution was carried out using acetate buffer (0.02M, pH 5.5) without NaCl, or containing 0.04, 0.15, or 0.5 M NaCl respectively, and a xylanase active fraction eluted by an acetate buffer without NaCl was collected.

2) Weakly basic ion-exchange chromatography

The obtained fraction in step 1 was absorbed on DEAE-TOYOPEARL 650S (Tosoh Co., Ltd.) in acetate buffer (0.02M, pH 6.0), step-wise elution was carried out using acetate buffer (0.02M, pH 5.5) without NaCl, or containing 0.2 M NaCl, and a xylanase-active fraction eluted by acetate buffer without NaCl was collected.

3) Strongly acidic ion-exchange chromatography

The obtained fraction in step 2 was absorbed on Mono S (Amersham Pharmacia Biotech Ltd.) in acetate buffer (0.1M, pH 3.5), linear gradient elution was carried out using acetate buffer (0.1M, pH 3.5) containing 0 to 0.05 M NaCl, and fractions showing xylanase activity were collected. Two fractions (FI, FII) which showed only xylanase activity were collected.

4) Gel filtration chromatography

The obtained fraction (FI) in step 3 was passed through Superdex 75 (Amersham Pharmacia Biotech Ltd.) using acetate buffer (0.05M, pH 3.5) plus 0.1 M NaCl, and fractions showing xylanase activity were collected and xylanase fraction thus eluted was purified xylanase I (mesophilic Xylanase I).

5) Gel filtration chromatography

The obtained fraction (FII) in step 3 was passed through Superdex 75 (Amersham Pharmacia Biotech Ltd.) using acetate buffer (0.05M, pH 3.5) plus 0.1 M NaCl, and fractions showing xylanase activity were collected. Xylanase fraction eluted first was purified Xylanase II (mesophilic xylanase II) and xylanase fraction eluted second was purified Xylanase III (mesophilic Xylanase III).

Through the above procedures, the enzymes were purified highly so that they gave single bands detected by protein-dyeing in native- and SDS-polyacrylamide gel electrophoreses.

EXAMPLE 3

To determine optimal pH at 30° C. of the purified Xylanases I, II, and III, obtained in said Example 2, saccharifying activity was determined using soluble xylan as a substrate. The result is shown in FIG. 1a, 1b, and 1c, respectively.

Figure 1B:
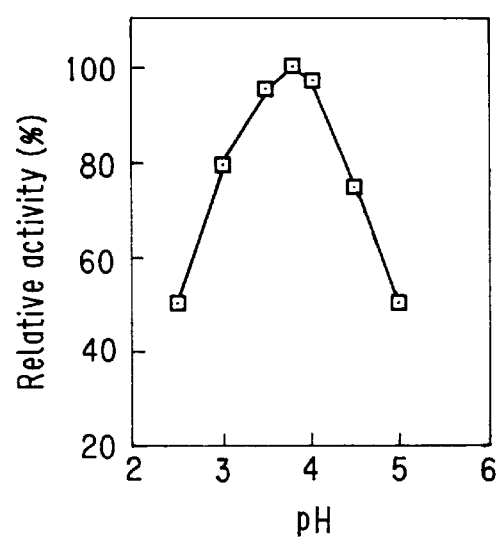
Figure 1C:
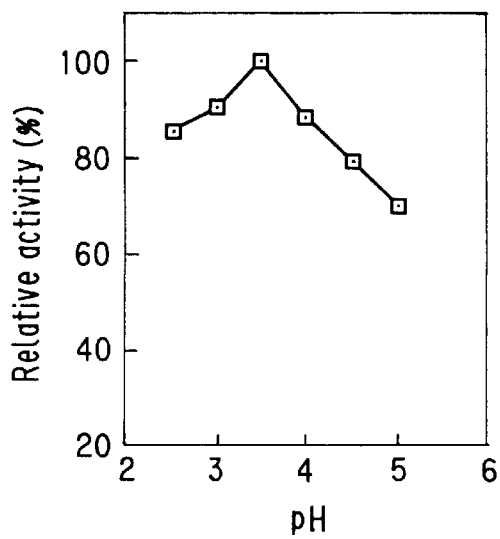

As shown in FIGS. 1a, 1b and 1c, these enzymes (purified Xylanases I, II, and III) showed maximum activity at pH 3.5, 3.8, and 3.5, respectively, when McIlvaine buffers were used.

Figure 2A:
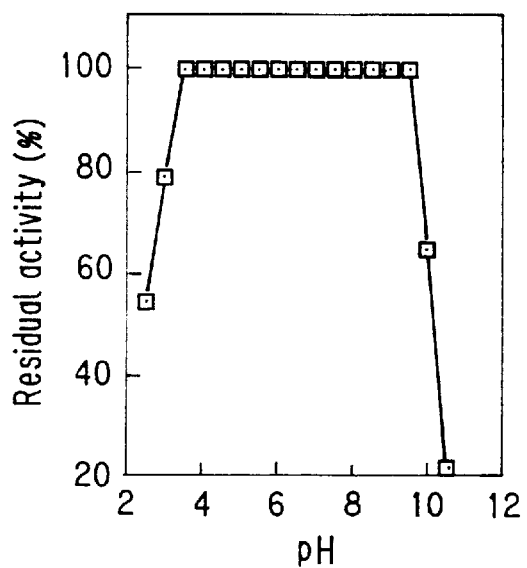
FIGS. 2a, 2b and 2c are graphs which show the pH-stability of the enzymes.
Figure 2B:
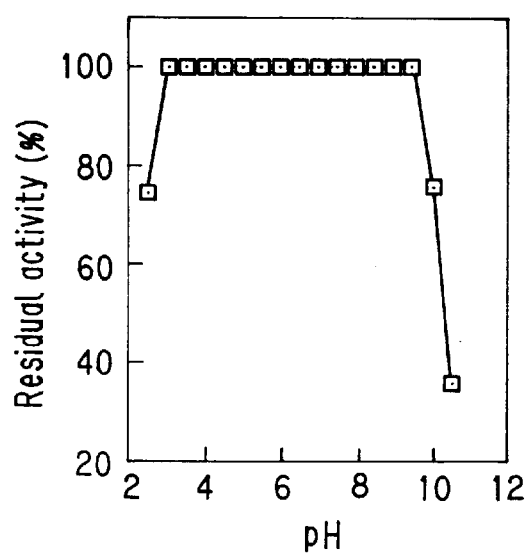
Figure 2C:
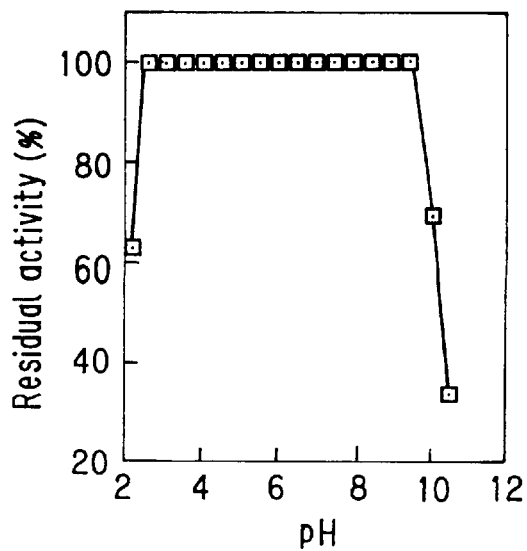

The pH-stability of these enzymes (purified Xylanases I, II, and III) after treatment of 25° C. for 2 hours is shown in FIG. 2a, 2b, and 2c, respectively.

As shown in FIGS. 2a, 2b and 2c, these enzymes (purified Xylanases I, II, and III) were stable at pH 3.5–9.5, 3.0–9.5, and 2.5–9.5, respectively.

EXAMPLE 4

To determine optimal temperature for action of the purified Xylanases I, II, and III, saccharifying activity was determined using soluble xylan as a substrate. The result is shown in FIG. 3a, 3b, and 3c, respectively.

Figure 3A:
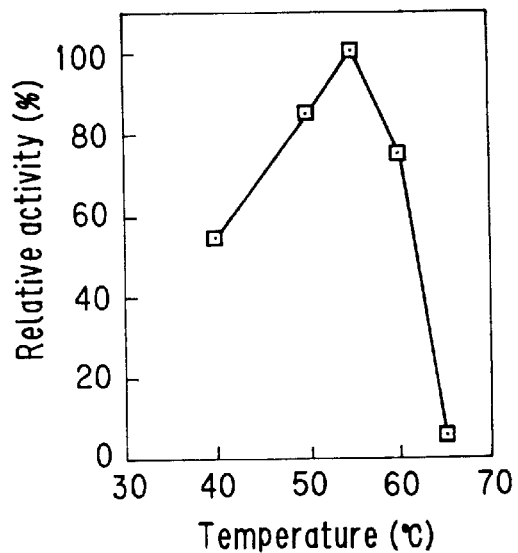
FIGS. 3a, 3b and 3c are graphs which show the optimal temperatures of the enzymes. indicate
Figure 3B:
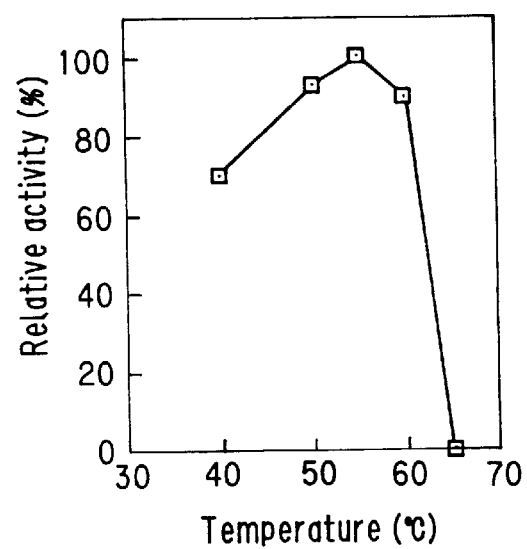
Figure 3C:
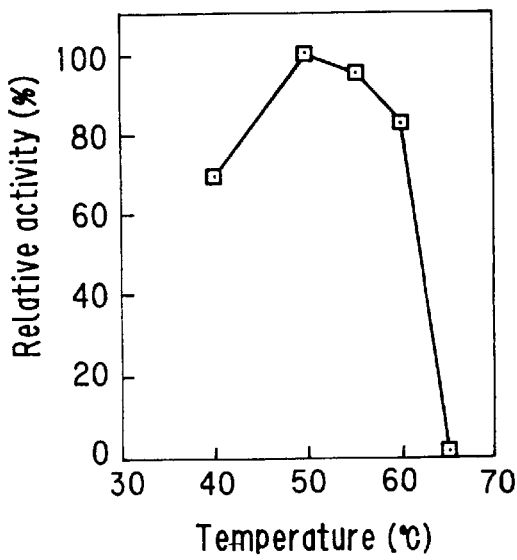

As shown in FIGS. 3a, 3b and 3c, these enzymes (purified Xylanases I, II, and III) showed optimal activity at 55° C., 55° C., and 50° C., each at pH 3.5.

Then temperature-stability of these enzymes (purified Xylanases I, II, and III) after treatment of pH 3.5 for 10 min was determined. The result is shown in FIG. 4a, 4b, and 4c, respectively.

Figure 4A:
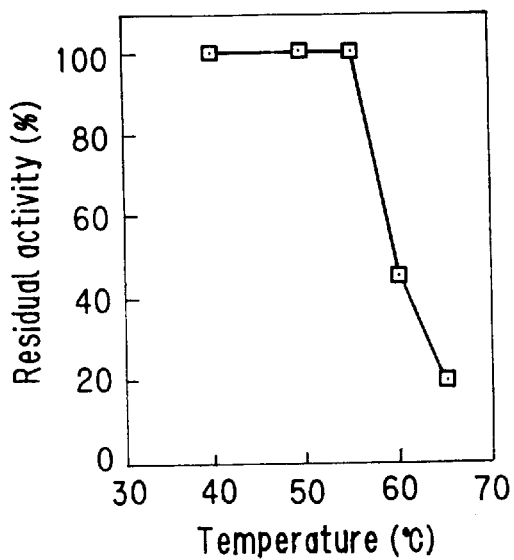
FIGS. 4a, 4b and 4c are graphs which show the temperature-stability of the enzymes FIGS. 4a, 4b and 4c indicate the ranges of temperature-stability for Xylanases I, II, and III, respectively.
Figure 4B:
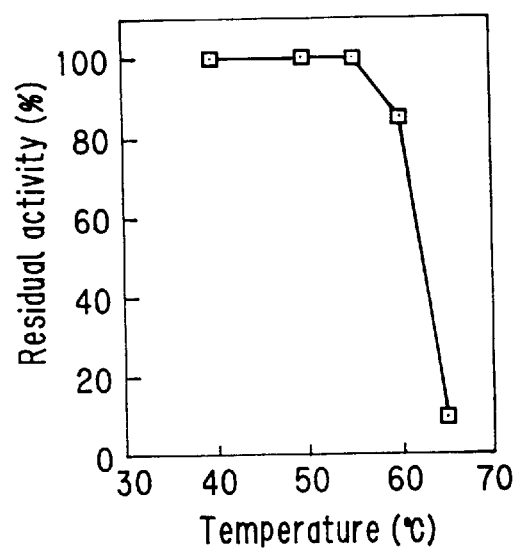
Figure 4C:
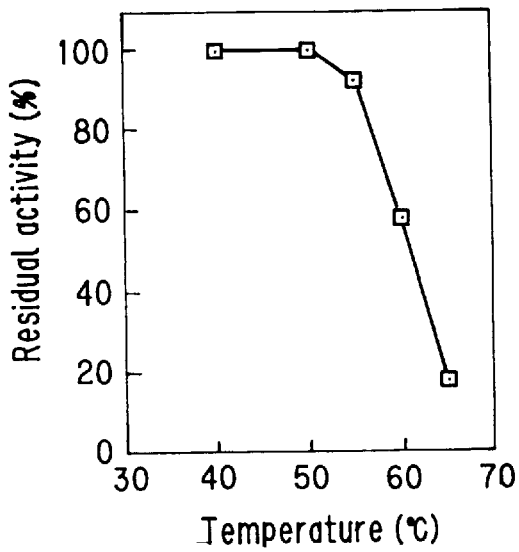

As shown in FIGS. 4a, 4b and 4c, these enzymes (purified Xylanases I, II, and III) were stable at ≦55° C., ≦55° C., and ≦50° C., respectively.

EXAMPLE 5

To determine each molecular weight of the purified Xylanases I, II, and III, obtained in Example 2, SDS-polyacrylamide gel electrophoresis was carried out using 12.5 wt. % gel at a constant current of 20 mA for 80 min at a room temperature. Result of the SDS-polyacrylamide gel electrophoresis is shown in FIG. 5.

Figure 5:
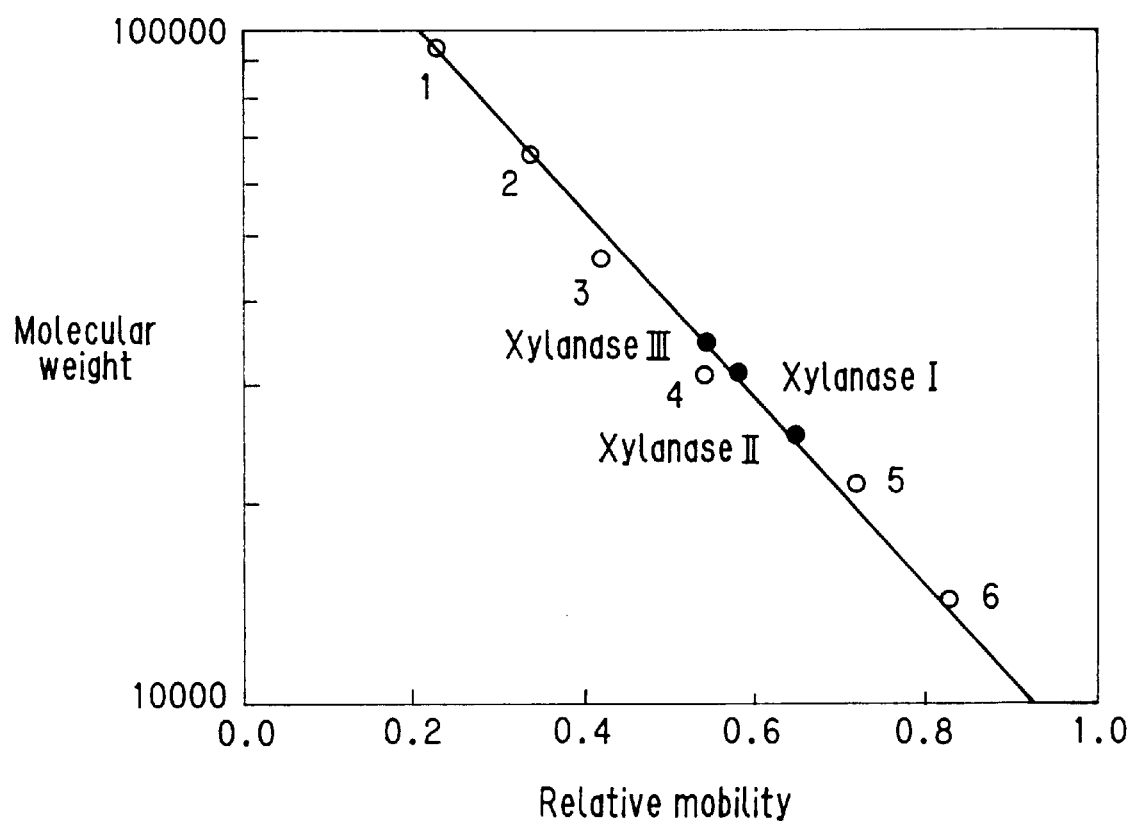
FIG. 5 is a graph which shows the results of a SDS-polyacrylamide gel electrophoresis to determine molecular weight of the enzymes.

From FIG. 5, molecular weights of the purified Xylanases I, II, and III were estimated to be ca. 30,000, ca. 25,500, and ca. 33,500, respectively.

Molecular weights of standard proteins for calibration (indicated by numbers 1, 2, 3, 4, 5, and 6 in FIG. 5) are as follows:

| 1 | Phosphorylase b | 97,400 |
| 2 | Serum albumin | 66,200 |
| 3 | Ovalalbumin | 45,000 |
| 4 | Carbonic anhydrase | 31,000 |
| 5 | Trypsin inhibitor | 21,500 |
| 6 | Lysozyme | 14,400. |

The enzymes, mesophilic xylanases according to the present are the main components in the xylanase system derived mold *Acremonium cellulolyticus*, and properties of the ere elucidated for the first time.

The enzymes (mesophilic Xylanases I, II, and III) have optimal temperatures for action at 55° C., 55° C., and 50° C., respectevely, i.e. at mesophilic temperature, at pH 3.5, and have activity in the neutral to acidic range.

Industrial Applicability

The enzymes, mesophilic xylanases according to the present invention are useful for food-processing, feed, silage, and other purposes.

What is claimed is:

1. A mesophilic xylanase I enzyme, derived from an *Acremonium celluloyticus* mold, having the following properties:

(a) an action: the enzyme hydrolyzes xylan non-specifically mainly into xylose, xylobiose and xylotriose, (b) a substrate specificity: the enzyme acts on xylan, (c) optimal pH and stable pH: the enzyme has an optimal pH at 3.5 and is stable at a pH of 3.5–9.5, at 25° C. for 2 hours as determined by saccharifying activity using soluble xylan as a substrate, (d) an optimal temperature for action at 55° C. as determined by saccharifying activity using soluble xylan as a substrate, (e) a temperature stability: the enzyme is stable at 55° C. or lower at a pH 3.5 for 10 minutes, (f) molecular weights of 30,000 as determined by SDS-polyacrylamide gel electrophoresis, and 69,500 when determined by gel filtration chromatography, and (g) specific activities of 112.1 U/mg-protein as determined by saccharifying activity for soluble xylan as a substrate, and 76.6 U/mg-protein as determined by saccharifying activity for insoluble xylan as a substrate.

2. A mesophilic xylanase II enzyme, derived from an *Acremonium cellulolyticus* mold, having the following properties:

(a) an action: the enzyme hydrolyzes xylan non-specifically mainly into xylose, xylobiose and xylotriose, (b) a substrate specificity: the enzyme acts on xylan, (c) optimal pH and stable pH; the enzyme has an optimal pH at 3.8 and is stable at a pH of 3.0–9.5, at 25° C. for 2 hours as determined by saccharifying activity using soluble xylan as a substrate, (d) an optimal temperature for action at 55° C. as determined by saccharifying activity using soluble xylan as a substrate, (e) a temperature stability: the enzyme is stable at 55° C. or lower at a pH of 3.5 for 10 minutes, (f) molecular weights of 25,500 as determined by SDS-polyacrylamide gel electrophoresis, and 58,000 when determined by gel filtration chromatography, and (g) specific activities of 86.1 U/mg-protein as determined by saccharifying activity for soluble xylan as a substrate, and 87.6 U/mg-protein as determined by saccharifying activity for insoluble xylan as a substrate.

3. A mesophilic xylanase III enzyme, derived from an *Acremonium cellulolyticus* mold, having the following properties:

(a) an action: the enzyme hydrolyzes xylan non-specifically mainly into xylose, xylobiose and xylotriose, (b) a substrate specificity: the enzyme acts on xylan, (c) optimal pH and stable pH: the enzyme has an optimal pH at 3.5 and is stable at a pH of 2.5–9.5, at 25° C. for 2 hours as determined by saccharifying activity using soluble xylan as a substrate, (d) an optimal temperature for action at 50° C. as determined by saccharifying activity using soluble xylan as a substrate, (e) a temperature stability: the enzyme is stable at 50° C. or lower at a pH 3.5 for 10 minutes, (f) molecular weights of 33,500 as determined by SDS-polyacrylamide gel electrophoresis, and 23,000 when determined by gel filtration chromatography, and (g) specific activities of 74.8 U/mg-protein as determined by saccharifying activity for soluble xylan as a substrate, and 101.5 U/mg-protein as determined by saccharifying activity for insoluble xylan as a substrate.

* * * * *